United States Patent [19]
Briskin et al.

[11] Patent Number: 6,063,313
[45] Date of Patent: May 16, 2000

[54] PROCESS FOR THE PREPARATION OF FINE PARTICLE PHARMACEUTICAL FORMULATIONS

[75] Inventors: Jacqueline E. Briskin, Buffalo Grove; Pramod K. Gupta, Gurnee; Claud Loyd, Beach Park; Robert W. Kohler, Waukegan; Susan J. Semla, Evanston, all of Ill.

[73] Assignee: Abbott Laboratories, Abbott Park, Ill.

[21] Appl. No.: 08/655,491

[22] Filed: May 30, 1996

Related U.S. Application Data

[63] Continuation of application No. 08/197,025, Jan. 16, 1994, abandoned.

[51] Int. Cl.[7] ............................. B29B 9/10; B29B 9/12
[52] U.S. Cl. ...................................................... 264/15
[58] Field of Search ............................................ 264/15

[56] References Cited

U.S. PATENT DOCUMENTS

| | | |
|---|---|---|
| 4,374,082 | 2/1983 | Hochschild ..................... 264/15 X |
| 4,686,231 | 8/1987 | Bender et al. . |
| 4,755,385 | 7/1988 | Etienne et al. . |
| 4,800,087 | 1/1989 | Mehta . |
| 5,002,774 | 3/1991 | Agrawala et al. . |
| 5,126,145 | 6/1992 | Evenstad et al. . |
| 5,169,645 | 12/1992 | Shukla et al. . |
| 5,173,496 | 12/1992 | Bruneau et al. . |
| 5,188,838 | 2/1993 | Deleuil et al. . |
| 5,292,900 | 3/1994 | Basha et al. . |

*Primary Examiner*—Leo B. Tentoni
*Attorney, Agent, or Firm*—Portia Chen; Dugal S. Sickert

[57] ABSTRACT

A process for preparing fine particle pharmaceutical formulations having improved throughput and producing greater uniformity of particle size. The process relates to adding to the dry components of the formulation prior to the steps of wetting, extrusion and spheronization, an extrusion aid material selected from pharmaceutically acceptable oils and waxes having a drop point between about 15° C. and 115° C.

7 Claims, No Drawings

PROCESS FOR THE PREPARATION OF FINE PARTICLE PHARMACEUTICAL FORMULATIONS

This application is a Continuation of application Ser. No. 08/197,025 filed on Jan. 16, 1994, now abandoned.

TECHNICAL FIELD

This invention relates pharmaceutical formulation processes. More particularly, the present invention concerns a process for preparing fine particle pharmaceutical formulations by extrusion/spheronization.

BACKGROUND OF THE INVENTION

Conventional processes for preparing fine particle pharmaceutical formulations by extrusion/spheronization involve the steps of blending the dry ingredients which make up the formulation, wetting the dry powdered blend, extruding the resulting wetted blend, and forming the extrudate into fine particles by spheronization.

Generally, the size of particles produced by the above method is limited to particle sizes ranging above about 0.5 mm. Moreover, the amount of water added in the wetting step must be carefully controlled. Excess water causes the extrudate in the extrusion step to take on the consistency of "mud" while too little water causes the wetted material to rupture the screens of the extrusion equipment. The result is that without very careful process control of the amount of water added to the formulation in the wetting step, batches may be unacceptable with attendant loss of time and/or money.

There is thus a need for a convenient, cost-effective and efficient method for making fine particle pharmaceutical formulations which overcome the disadvantages inhenent in prior art methods.

SUMMARY OF THE INVENTION

This invention provides a process having improved throughput for preparing fine particle pharmaceutical formulations which exhibit improved uniformity of particle size and performance characteristics such as drug release. The process is useful for the preparation of formulations comprising fine particles having particle sizes ranging between about 0.05 mm and about 1 mm which may be used as a sprinkle formulation for administering a therapeutically active compound to a patient. The particles may also be used in suspensions, and as a component of tablets and capsules.

The process for the preparation of the fine particle pharmaceutical formulations comprises a) adding to the dry components of the formulation an extrusion aid material, wherein the extrusion aid material is selected from pharmaceutically acceptable oils and waxes having a drop point ranging between about 15° C. and 115° C.; b) thoroughly blending the dry mixture; c) wetting the mixture resulting from step b) to form a granular mixture of the formulation; d) extruding the granular mixture through a mesh; e) spheronizing the extrudate; and f) drying the fine particles resulting from step e) to form a fine particle formulation.

DETAILED DESCRIPTION OF THE PREFERRED EMBODIMENTS

The present invention provides a method for making fine particulate formulations that can be used to administer therapeutically active compounds to a patient The process has three distinct advantages over prior art processes for making fine particle formulations: first, the amount of wetting agent (e.g. water or water containing one or more additives) added to the blend of dry ingredients in the wetting step does not need to be as carefully controlled; second, the process is capable of producing fine particle formulations in which the particle size may be less than 0.5 mm; and third, the particle size and the performance characteristics of the fine particle formulations produced is more uniform than that resulting from prior art processes.

The formed particles may contain one or more therapeutically active compounds, including pharmaceutically acceptable salts, esters, amides and prodrugs. The therapeutically active compounds may be any therapeutically active compounds for which oral administration is desired. However, the selected therapeutically active compound should be compatible with the selected extrusion aid material and any excipients. Some examples of therapeutically active compounds that may be used in the present invention include, but are not limited to: $\alpha$-adrenergic agonists such as clonidine and pseudoephedrine; analgesics such as acetaminophen, aspirin, and ibuprofen; antianginals such as verapamil and nifedipine; antibacterials (antibiotics) such as penicillin, erythromycin, tetracycline, amoxicillin, trimethoprim and clarithromycin; antidepressants such as imipramine; antiinflammatory agents such as indomethacin and zileuton; antimigrane agents such as ergotamine; antineoplastics such as methotrexate and etoposide; antivirals such as acyclovir and zidovudine; calcium channel blockers such as diltiazem and verapamil; cardiotonic agents such as digoxin; expectorants such as quaifenesin; bronchodialators such as theophylline; antihypertensives such as methyldopa; antihistamines such as diphenhydramine, dextromethorphan, phenyltoloxamine, brompheniramine, and chlorpheniramine; diuretics such as furosemide and hydrochlorothiazide; antiepileptics such as tiagabine, phenytoin sodium, divalproex sodium, trimethadione, and paramethadione; central nervous system stimulators such as caffeine and pemoline; decongestants such as phenylepinephrine and phenylephrine; inorganic salts such as potassium chloride and calcium carbonate; enzymes such as pancreatic enzyme; and vitamins.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with the tissues of patients without undue toxicity, irritation, allergic response, and the like, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate, mesylate, glucoheptonate, lactiobionate, and laurylsulphonate salts and the like. These may include cations based on the alkali and alkaline earth metals, such as sodium, lithium, potassium, calcium, magnesium, and the like, as well as non-toxic ammonium, quaternary ammonium and amine cations including, but not limited to, ammonium, tetramethylammonium, tetraethylammonium, methylamine, dimethylamine, trimethylamine, triethylamine, ethylamine and the like (cf. S. M. Berge, et al., "Pharmaceutical Salts," *J. Pharm, Sci.*, 66: 1–19 (1977).

Examples of pharmaceutically acceptable non-toxic esters of the compounds of this invention include $C_1$ to $C_4$ alkyl esters wherein the alkyl group is a straight or branched chain. Acceptable esters also include $C_5$ to $C_7$ cycloalkyl esters as well as arylalkyl esters such as, but not limited to, benzyl, phenyethyl, phenylpropyl and the like. $C_1$ to $C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "pro-drug" referes to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol. 14 of the A.C.S. Symposium Series, and in *Bioreversible Carriers in Drug Design*, ed. Edward B. Roche, American Pharmaceutical Association and Pergamon Press, 1987.

Typically the therapeutically active agent is present in the formulation in an amount up to about 90 percent by weight of the entire composition.

The extrusion aid is selected so that it does not detrimentally interact with the therapeutically active compound or any excipients and so that it is biocompatible. Preferably, the extrusion aid is a material having a drop point in the range of 15° C. to about 115° C. By the term "drop point" as used throughout this specification and claims is meant the temperature at which the material melts or softens to the point where it forms a drop and falls from the thermometer bulb used to take the drop point measurement.

The particular extrusion aid material or mixture of extrusion aid materials that may be used are also selected with regard to the properties of the therapeutically active compound For example, if the therapeutically active compound degrades at a certain temperature, the extrusion aid material having a melting or softening temperature below the compound's degradation temperature is preferred. Some examples of suitable extrusion aid materials that may be used in the process of the present invention include, but are not limited to: fats, fatty acid esters, hydrogenated vegetable oils, saturated polyglycolized glycerides of hydrogenated vegetable oils, polyethylene glycol esters of hydrogenated vegetable oils such as Lubritab®, Gelucires® and high molecular weight polyethylene glycols. Other compounds having the above referenced properties, which could be used a extrusion aid materials include, but are not limited to, waxes such as carnauba wax, glyceryl esters of aliphatic acids, especially stearic, palmitic and oleic acids, cocoa butter, phospholipids such as lecithins, and sterols such as cholesterol.

The most preferred extrusion aid materials are Lubritab®, a hydrogenated vegetable oil NF obtainable form the Mendell Co. Carmel, N.Y., Compritol® 888 ATO, glyceryl behenate NF obtainable from Gattefosse, Westwood, N.J., and wax, preferably micronized wax. Preferably, the extrusion aid material is present in the formulations made by the process of this invention in amounts ranging between about 1 percent by weight to about 75 percent by weight based upon the total weight of the formulation.

Fine particle formulations prepared by the process of the present invention may take the form of so-called "sprinkle" formulations which are packaged in a paper, plastic, or foil cachet or in pull-apart capsules. The patient utilizes the formulation by tearing open the cachet or by pulling apart the capsule and then sprinkles the drug formulation over a food for ingestion. In another application, the fine particles produced by the method of the present invention may be sealed inside a capsule. Alternatively, the fine particles produced by the process of this invention may be dispersed within a convention tablet formulation.

The formulations made by the process of this invention may thus contain ingredients in addition to the active therapeutic agent and the extrusion aid material which are chosen to tailor-make the final formulation for its intended purpose. For example, disintegrating agents such as starch, cross-linked polyvinylpyrrolidone (Crospovidone), cross-linked cellulose (Croscarmelose), and sodium starch glycolate may be added to enhance the fast disintegration and dissolution of the fine particles.

Conversely, for rapidly dissolving drugs, conventional binding agents may be added to the formulations made by the process of this invention to retard too-rapid dissolution. Suitable binder agents include polyvinylpyrrolidone (such as Povidone 30 and Povidone 90), carboxymethyl celluloses, and hydroxymethyl celluloses.

In some cases, fillers such as microcrystalline cellulose and lactose may be added to formulations made by the process of this invention. Microcrystalline cellulose extrudes well and undergoes spheronization well to aid in forming fine particles by the process of this invention and is a preferred filler.

The formulation may also include various excipients which are generally chosen from excipients that are conventionally used in solid compositions, such as tablets. Preferred excipients include lactose, mannitol, microcrystalline cellulose (Avicel®) and vitamin E. The excipients, including fillers, may be present in the composition in an amount of about 75 percent to 90 percent by weight based upon the weight of the formulation.

The particles can also be coated, for example, with an enteric coating or a coating which masks any unpleasant taste of the ingredients of the particulate, including masking the taste of therapeutically active compounds, granulating materials or any excipients. A coating may also be used to provide for the controlled release of the therapeutically active compounds from the fine particulate.

The fine particle produced by the disclosed method have the advantages that they have an improved mouth feel; i.e., the particle do not feel gritty or abrasive to the patient. The surface of the particles are also more uniform than particles produced by prior art methods and therefore are more readily coated, if desired. Similarly, the fine particles produced by the present method have improved chemical stability of the therapeutically active compound.

It is also recognized that there are other applications for which the fine particles of the present invention may be useful. For example, a fine particulate may be useful in agriculture to deliver a therapeutically active compound, a fertilizer, or other agents to plants. It is intended that other such applications which employ the fine particles of the p resent invention fall within the scope of this invention.

General Process Method

In practicing the process of the present invention, the following general procedure is used. First, all of the dry ingredients are thoroughly blended. On a small scale the dry blending may be carried out in stainless steel bowls. For larger quantities, dry mixing of the ingredients may be conveniently carried out in a twin-shell belnder of the Patterson-Kelley type. Planetary mixers, for example a Glen mixer or a Hobart mixer, are also conveniently used.

The resulting dry mixture is then wetted by addition of sufficient wetting fluid (e.g. water) to the dry mixture to obtain a granulated solid having the consistency of damp snow or brown sugar. The wetting step is carried out in batches in mixers of the type described above or, conventional equipment which permits the continuous uniform moisturization of the dry blend.

The granulated powder is then fed by auger to conventional extruding equipment where the solid is extruded at high shear through screens of the appropriate mesh size to form threads of the drug formulation. Typical of extrusion equipment for this step is the Model EXDCS-10 Extruder manufactured by Fuji Paudal Co., Ltd. The product at this stage of the process is in the form of long strands of spaghetti-like drug formulation, with the strands having the diameter of the extrusion mesh.

The strands of drug formulation from the previous step are collected and fed to a spheronizing apparatus, typified by the Marumerizer, manufacterued by the Fuji Paudal Co. Ltd. or t he CF Granulator manufactured by the Vector Corporation. Microcrystalline cellulose or other excipients may be added to the formulation mixture at this point to dust the material to prevent agglomeration. The spheronizer tumbles the spaghetti-like strands of drug formulation, breaking them up into spheroids of the general diameter of the strands or smaller.

The spheroids of drug formulation produced in the prior step are then dried in a conventional fluid bed dryer such as that manufactured by Niro, Inc. In the final step, the particles are passed through seives for sizing. The fine particles may then be incorporated into conventional pharmaceutical formulations as cachets, capsules, or by formulation into tablets or caplets.

EXAMPLE 1

Effect of the Presence or Absence of an Extrusion Aid Material on the Extursion of Pharmaceutical Formulations and the Uniformity of Particle Size In this example, several formulations were prepared both with and without an extrusion aid (glyceryl behenate). The various formulations compositions and the results upon extrusion appear in Table 1.

Examination of the data in Table 1 shows that when an extrusion aid is included in the formulations prepared by the process of the present invention, smooth extrusion of the formulation follows, even at the very small extrusion mesh size of 0.3 mm. For examples in formulation "1a" which included clarithromycin (a therapeutic agent characteristically difficult to extrude), even though a waxy material, Carbopol, was included in the formulation, the extrusion apparatus screens ruptured immediately after extrusion was begun. In contrast, when the same formulation included the preferred extrusion aid, glyceryl behenate, the extrusion screens flexed but did not rupture. Moreover, greater than 70% of the fine particles which were produced were in the desired range of 40–60 mesh.

The drug zileuton is characteristically more easily extruded, but in formulation "1c" which lacked an extrusion aid material, the screens of the extrusion apparatus ruptured after a brief period of successful extrusion. In contrast, in formulations "1d"–"1g" which included hydrogentaed vegetable oil as an extrusion aid material, successful extrusion of the drug formulation was achieved.

TABLE 1

| Formulation | Composition (% by Weight) | Screen Size | Results |
|---|---|---|---|
| 1a | Clarithromycin (57.9) Povidone K90 (7.4) Carbopol (34.7) | 0.3 mm | Screens ruptured immediately; no particles obtained |
| 1b | Carithromycin (43.4) Povidone K90 (5.5) Carbopol (26.0) Hydroxypropyl cellulose (5.0) Glyceryl behenate (10.0) Microcrystalline cellulose (10.0) | 0.3 mm | Screens flexed but did not rupture; 70.4% yield of 40–60 mesh particles obtained |
| 1c | Zileuton (95) Povidone K90 (5) | 0.3 mm | Much flexing of extrusion screens observed; screens finally ruptured |
| 1d | Zileuton* (82) Povidone K90 (5) Microcrystalline cellulose (10.0) Hydrogenated vegetable oil (3) | 0.3 mm | Extrusion screens flexed but did not break |
| 1e | Zileuton* (82) Povidone K90 (5) Microcrystalline cellulose (10.0) Hydrogenated vegetable oil (3) | 0.3 mm | Extrusion screens flexed but did not break |
| 1f | Zileuton* (72) Povidone K90 (5) Microcrystalline cellulose (20.0) Hydrogenated vegetable oil (3) | 0.3 mm | Extrusion screens flexed but did not break |
| 1g | Zileuton* (72) Povidone K90 (5) Microcrystalline cellulose (20.0) Hydrogenated vegetable oil (3) | 0.3 mm | Extrusion screens flexed but did not break |
| 1h | Zileuton* (50) Povidone K30 (5) Sodium starch glycolate (5) Microcrystalline cellulose (40) | 0.3 mm | Extrusion screens flexed but did not break |
| 1i | Zileuton* (50) Povidone K30 (5) Sodium starch glycolate (5) Microcrystalline cellulose (30) Compitrol ® (10) | 0.3 mm | No significant flexing of extrusion screens |

*Zileuton is N-hydroxy-N-2-((benzo[b]thien-2-yl)ethyl)urea

EXAMPLE 2

Effect of the Inclusion of an Extrusion Aid Material on the Role of Wetting Fluid (e.g. Water) in Fine Particle Formulations In this example, several fine particle pharmaceutical formulations were prepared using zileuton (i.e. N-hydroxy-N-2-((benzo[b]thien-2-yl)ethyl)urea), excipients, disintegrating agents, binders, water, and the preferred extrusion aid material (glyceryl behenate) in accordance with the present invention. The compositions contained water in amounts ranging between 520 ml per kg of formulation (34.2% by weight) to 760 ml per kg of formulation (43.2% by weight). The formulation compositions are presented in Table 2.

TABLE 2

| Formulation Component | Composition (% by Weight) | | | | | | | |
|---|---|---|---|---|---|---|---|---|
| | 2a | 2b | 2c | 2d | 2e | 2f | 2g | Mean |
| Zileuton* | 50 | 50 | 50 | 50 | 50 | 50 | 50 | |
| Hydroxypropyl cellulose | 5 | 5 | 5 | 5 | 5 | 5 | 5 | |
| Sodium starch glycolate | 5 | 5 | 5 | 5 | 5 | 5 | 5 | |
| Glyceryl behenate | 5 | 5 | 5 | 5 | 5 | 5 | 5 | |
| Avicel ™ PH 101 | 35 | 35 | 35 | 35 | 35 | 35 | 35 | |
| Water (ml/kg) | 520 | 560 | 600 | 640 | 680 | 720 | 760 | |
| % by weight | 34.2% | 35.9% | 37.5% | 39.0% | 40.5% | 41.9 | 43.2 | |
| % Particles in 30–60 mesh | 96.4 | 96.3 | 98.5 | 99.0 | 97.2 | 97.6 | 92.9 | 96.8 |
| % Drug released in 1 hour | 53.6 | 50.1 | 47.8 | 46.4 | 48.4 | 47.4 | 46.6 | 48.8 |
| % Drug released in 2 hours | 75.2 | 72.9 | 69.9 | 68.7 | 70.5 | 69.3 | 70.1 | 70.9 |
| % Drug released in 4.5 hours | 95.7 | 95.0 | 93.7 | 93.1 | 94.5 | 93.2 | 93.7 | 94.1 |
| Release rate (%/√hr) | 59.7 | 60.6 | 58.6 | 57.7 | 59.2 | 57.5 | 58.5 | 58.8 |

*Zileuton is N-hydroxy-N-2-((benzo[b]thien-2-yl)ethyl)urea

In each of the formulations presented in Table 2, the compositions were extruded successfully through a 0.5 mm mesh screen to produce fine particle formulations having substantially uniform particle size. The generally accepted teachings in the art are that the amount of wetting fluid (e.g. water) contained in the formulation at the time of extrusion is a critical factor in determining success of extrusion and microparticle spheroid size and shape (cf. L. C. Wan, et al. report in the *International Journal of Pharmaceutics*, 96: 59–65 (1993)). However, the data shown in Table 2 indicate that when an extrusion aid is incorporated into formulations made in accordance with the process of the present invention, the amount of wetting fluid (e.g. water) employed in the wetting step need not be critically controlled to successfully produce fine particle formulations. The data in Table 2 show that for formulations "2a"–"2g", there is substantial uniformity of the particle size of the batches produced by the method of this invention as well as uniformity in drug release profile. For example, all formulations shown in Table 2 had at least 95% particles in the desired size range of 30–60 mesh. Also, all formulations demonstrated consistent drug release from batch to batch. These data indicate that use of the method of the present invention results in fewer batches being rejected with considerable savings in cost and efficiency of processing.

The foregoing examples have been provided to enable one skilled in the art to more fully understand the invention, but are not intended to be read as limiting the scope of the invention as it is defined by the appended claims.

We claim:

1. A process for the preparation of fine particle pharmaceutical formulations comprising the steps of
   a) adding to the dry components of the formulation an extrusion aid material, wherein the extrusion aid material is a pharmaceutically acceptable oil or a wax having a drop point ranging between about 15° C. and 115° C.;
   b) thoroughly blending the dry mixture;
   c) wetting the mixture resulting from step b) to form a granular mixture of the formulation;
   d) extruding the granular mixture through a mesh to form an extrudate;
   e) spheronizing the extrudate; and
   f) drying the fine particles resulting from step e) to form a fine particle formulation.

2. The process of claim 1 wherein said extrusion aid is selected from the group consisting of fats, fatty acid esters, saturated polyglycolized glycerides of hydrogenated vegetable oils, polyethylene glycol esters of hydrogenated vegetable oils, high molecular weight polyethylene glycols, waxes, glyceryl esters of aliphatic acids, cocoa butter, phospholipids and sterols, and mixtures thereof.

3. The process of claim 1 wherein said extrusion aid is added to the components of the pharmaceutical formulation in an amount ranging between about 1 percent by weight to about 75 percent by weight based upon the total weight of the fine particle formulation.

4. The process of claim 2 wherein said extrusion aid is selected from the group consisting of glyceryl behenate, hydrogenated vegetable oil, and wax.

5. The process of claim 4 wherein said extrusion aid is glyceryl behenate.

6. The process of claim 2 wherein said extrusion aid is wax.

7. The process of claim 1 wherein said fine particle formulation has a particle size below about 1 mm.

* * * * *

UNITED STATES PATENT AND TRADEMARK OFFICE
CERTIFICATE OF CORRECTION

PATENT NO. : 6,063,313   Page 1 of 1
DATED : May 16, 2000
INVENTOR(S) : Jacqueline E. Briskin et al.

It is certified that error appears in the above-identified patent and that said Letters Patent is hereby corrected as shown below:

Column 1,
Line 35, replace "inhenent in" with -- inherent in --.

Column 3,
Line 48, replace "pound For" with -- found. For --.
Line 67, replace "vegetable oil NF" with -- vegetable oil, NF --.
Line 67, replace "form" with -- from --.

Column 4,
Line 24, replace "(Crospovidone)" with -- (Crospovidone® ) --.
Line 26, replace "(Croscarmelose)" with -- (Croscarmelose® ) --.
Line 33, replace "Povidone 30 and Povidone 90" with -- Povidone 30® and Povidone 90® --.

Signed and Sealed this

Nineteenth Day of March, 2002

Attest:

JAMES E. ROGAN
*Director of the United States Patent and Trademark Office*

*Attesting Officer*